US009818423B2

(12) United States Patent
Kim

(10) Patent No.: US 9,818,423 B2
(45) Date of Patent: Nov. 14, 2017

(54) METHOD OF IMPROVING SOUND QUALITY AND HEADSET THEREOF

(71) Applicant: INDUSTRIAL BANK OF KOREA, Seoul (KR)

(72) Inventor: Eundong Kim, Uiwang (KR)

(73) Assignee: ORFEO SOUNDWORKS CORPORATION, Anyang-si (KR)

( * ) Notice: Subject to any disclaimer, the term of this patent is extended or adjusted under 35 U.S.C. 154(b) by 0 days.

(21) Appl. No.: 15/318,725

(22) PCT Filed: Aug. 31, 2015

(86) PCT No.: PCT/KR2015/009156
§ 371 (c)(1),
(2) Date: Dec. 14, 2016

(87) PCT Pub. No.: WO2017/026568
PCT Pub. Date: Feb. 16, 2017

(65) Prior Publication Data

US 2017/0249954 A1 Aug. 31, 2017

(30) Foreign Application Priority Data

Aug. 13, 2015 (KR) ........................ 10-2015-0114455

(51) Int. Cl.
*A61F 11/06* (2006.01)
*G10K 11/16* (2006.01)
(Continued)

(52) U.S. Cl.
CPC ...... *G10L 21/0205* (2013.01); *G10L 21/0232* (2013.01); *G10L 25/84* (2013.01);
(Continued)

(58) Field of Classification Search
CPC .... H04R 1/1083; H04R 1/1016; H04R 3/005; H04R 3/04; G10L 21/0205; G10L 2021/02166; G10L 21/0232; G10L 25/84
(Continued)

(56) References Cited

U.S. PATENT DOCUMENTS

2014/0010378 A1* 1/2014 Voix .................... H04R 1/1083 381/57

FOREIGN PATENT DOCUMENTS

JP 05-284589 A 10/1993
JP 2007-228344 A 9/2007
(Continued)

*Primary Examiner* — Paul S Kim
(74) *Attorney, Agent, or Firm* — Patent Office of Dr. Chung Park

(57) ABSTRACT

Disclosed is a headset including at least one in-ear microphone; at least one out-ear microphone; a control unit including an in-ear signal processing module for extracting low frequency components from a signal sensed through the in-ear microphone, an out-ear signal processing module for extracting high frequency components from a signal sensed through the out-ear microphone, and a mixing module for mixing the extracted low frequency components and high frequency components and outputting the mixed signal; and a communication unit for transmitting the signal output from the mixing module of the control unit to an external device, and sound quality can be improved by removing noises in a voice signal of a user transferred through the headset and creating a signal close to the voice of the user.

5 Claims, 5 Drawing Sheets

(51) Int. Cl.

| | |
|---|---|
| ***G10L 21/02*** | (2013.01) |
| ***G10L 21/0232*** | (2013.01) |
| ***G10L 25/84*** | (2013.01) |
| ***H04R 1/10*** | (2006.01) |
| ***H04R 3/04*** | (2006.01) |
| ***H04R 3/00*** | (2006.01) |
| *G10L 21/0216* | (2013.01) |

(52) U.S. Cl.
CPC ......... *H04R 1/1016* (2013.01); *H04R 1/1083* (2013.01); *H04R 3/005* (2013.01); *H04R 3/04* (2013.01); *G10L 2021/02166* (2013.01)

(58) Field of Classification Search
USPC .......................................................... 381/71.6
See application file for complete search history.

(56) References Cited

FOREIGN PATENT DOCUMENTS

| | | |
|---|---|---|
| KR | 10-2012-0091454 A | 8/2012 |
| KR | 10-2013-0054898 A | 5/2013 |
| KR | 10-2013-0101152 A | 9/2013 |

* cited by examiner

METHOD OF IMPROVING SOUND QUALITY AND HEADSET THEREOF

TECHNICAL FIELD

The present invention relates to a method of improving sound quality of a voice signal transferred through a headset, and more specifically, to a method of improving sound quality and a headset employing the method, in which a sound is processed to be similar to a real voice of a user when the user connects the headset to a mobile device and communicates while wearing the headset.

BACKGROUND ART

Although it is general in the past to communicate while holding a cellular phone in a hand, a headset is widely used to listen to music or communicate as smart phones are distributed.

A headset generally is manufactured in the form of an earphone or a headphone and provided with two speakers and a microphone.

A user plays back and listens to music using a smart phone while wearing a headset, and if the phone rings, the user selects a communication function and communicates while wearing the headset. The microphone does not work during the user listens to music, and if the communication function is selected, the smart phone stops playback of the music and operates the microphone to transfer user's voice to a communication counterpart. Simultaneously, the smart phone reproduces counterpart's voice through the speakers so that the user may hear the voice.

Generally, a lot of ambient noises are mixed in a voice signal captured through an out-ear microphone attached to the headset, and thus communication quality is lowered.

In order to provide a headset capable of solving the noise problem and further convenient to wear, an in-ear microphone is used, in which a microphone is positioned in an ear of the user by installing the microphone in the head of the earphone while maintaining the outer appearance of a wired or wireless earphone as is.

If the in-ear microphone is used, although the ambient noises are blocked, the voice transferred through the ear canal almost does not contain high frequency components, and a large portion of the voice is low frequency components, and thus the voice of the microphone is quite different from the real voice of the user.

DISCLOSURE OF INVENTION

Technical Problem

Therefore, the present invention has been made in view of the above problems, and it is an object of the present invention to provide a method of improving sound quality of a voice signal transferred through the microphone of a headset using both an in-ear microphone and an out-ear microphone, and a headset thereof.

Technical Solution

To accomplish the above object, according to one aspect of the present invention, there is provided a headset comprising: at least one in-ear microphone; at least one out-ear microphone; a control unit including an in-ear signal processing module for extracting low frequency components from a signal sensed through the in-ear microphone, an out-ear signal processing module for extracting high frequency components from a signal sensed through the out-ear microphone, and a mixing module for mixing the extracted low frequency components and high frequency components and outputting the mixed signal; and a communication unit for transmitting the signal output from the mixing module of the control unit to an external device.

The at least one out-ear microphone may include a first out-ear microphone provided in a first head of the headset and a second out-ear microphone provided in a second head of the headset, and the out-ear signal processing module may include a beamforming module for performing a beamforming process of sensing only a voice emitted from a user by removing a signal having a time difference from two signals output from the first out-ear microphone and the second out-ear microphone.

The out-ear signal processing module may further include a noise suppression module for removing noises from a signal output from the beamforming module.

The in-ear signal processing module may include a voice activity detection (VAD) module for determining, if there is a signal sensed through the in-ear microphone, that a user is emitting a voice, and the noise suppression module may operate only when it is determined by the VAD module that the user is emitting a voice.

The in-ear signal processing module may include a voice activity detection (VAD) module for determining, if there is a signal sensed through the in-ear microphone, that a user is emitting a voice, and the mixing module may operate only when it is determined by the VAD module that the user is emitting a voice.

The in-ear signal processing module may include an enhancing module for balancing a signal by increasing a high frequency sound and decreasing a low frequency sound of a signal output from the in-ear microphone before the low frequency components are extracted.

According to another aspect of the present invention, there is provided a method of improving sound quality of a headset provided with at least one in-ear microphone and at least one out-ear microphone, the method comprising the steps of: extracting low frequency components from a signal sensed through the in-ear microphone; extracting high frequency components from a signal sensed through the out-ear microphone; the mixing and outputting the extracted low frequency components and high frequency components.

Advantageous Effects

According to the present invention as described above, sound quality can be improved by removing noises in a voice signal of a user transferred through the headset and creating a signal close to the voice of the user.

LIST OF REFERENCE NUMERALS

Figure 1:
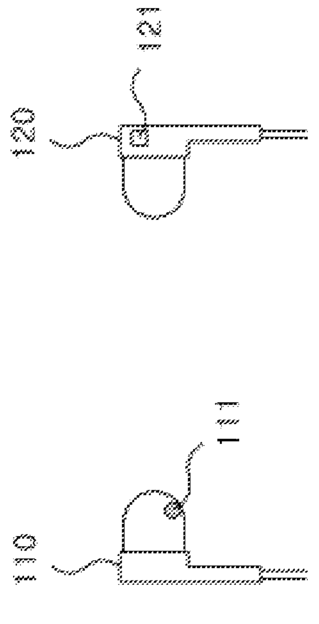
FIG. 1 is a view showing the outer appearance of a headset according to an embodiment of the present invention.

200, 500: Headset
210: External device
220, 520: Control unit
230, 530: Communication unit
110, 240, 410, 540: First head
120, 250, 420, 550: Second head
111, 241, 411, 541: In-ear microphone
242, 252, 542, 552: Speaker unit
121, 251, 412, 422, 543, 551: Out-ear microphone
310, 610: In-ear signal processing module
320, 620: Out-ear signal processing module (320)
330, 630: Mixing module
611: Enhancing module
612: Low-frequency signal extraction module
613: VAD module
621: Beamforming module
622: NS module
623: High-frequency signal extraction module

BEST MODE FOR CARRYING OUT THE INVENTION

The terminology used herein will be described briefly, and the present invention will be described in detail.

The terminology used herein is defined in consideration of the function of corresponding components used in the present invention and may be varied according to users, operator's intention, or practices. In addition, an arbitrary defined terminology may be used in a specific case and will be described in detail in a corresponding description paragraph. Therefore, the terminology used herein is for the purpose of describing particular embodiments only and is not intended to be limiting of the invention.

Throughout the specification, unless explicitly described to the contrary, the word "comprise" and variation such as "comprises" or "comprising" will be understood to imply the inclusion of stated elements but not the exclusion of any other elements. In addition, terms such as "unit," "means," "part," "member," etc., which are described in the specification, means a unit of a comprehensive configuration that performs at least one function or operation, and this may be implemented in hardware or software or implemented as a combination of hardware and software.

The present invention will be described more fully hereinafter with reference to the accompanying drawings, in which exemplary embodiments of the invention are shown. As those skilled would realize, the described embodiments may be modified in various different ways, all without departing from the spirit or scope of the present invention. Accordingly, the drawings and description are to be regarded as illustrative in nature and not restrictive, and like reference numerals designate like elements throughout the specification.

FIG. 1 is a view showing the outer appearance of a headset according to an embodiment of the present invention.

Referring to FIG. 1, a headset according to the present invention includes a first head 110 and a second head 120 worn in the ears of a user, in which a speaker unit (not shown) is provided in each of the two heads 110 and 120. In addition, an in-ear microphone 111 is disposed in the first head 110 of the two heads, and an out-ear microphone 112 is disposed in the second head 120. In some embodiments, the in-ear microphone 111 and the out-ear microphone 112 may be installed in the same head.

Although a voice of a person goes out of the mouth, it is also transferred inside the ears through the tympanic membranes. This corresponds to a case in which if a person speaks while closing the ears, the person may hear his or her own voice. Accordingly, if the in-ear microphone 111 is installed in the earphone head 110 so that the microphone is positioned in an inner portion of the ear when the person wears the earphone, only the voices transferred to the inner portion of the ear can be transferred while blocking external noises.

Like this, the in-ear microphone 111 is a microphone positioned inside the ear canal of a user when the user wears the in-ear microphone 111. The in-ear microphone 111 may be disposed to be tightly attached to the ear canal of the user or may be disposed toward the inside of the ear canal of the user when user wears the in-ear microphone 111. If the in-ear microphone 111 is disposed toward the inside of the ear canal without being tightly attached to the ear canal of the user, the voices transferred to the inner portion of the ear may be captured more efficiently.

Since a signal received through the in-ear microphone 111 almost does not contain high frequency components in the voice of a person and only low frequency components remain, a sound different from the real voice of the person is heard. Accordingly, in the present invention, the in-ear microphone 111 is used to capture low frequency sound from the voice signal. In addition, since a signal coming into the in-ear microphone 111 is only the voice of the person and the external noises are blocked, whether the person is in speaking can be confirmed if the in-ear microphone 111 is used.

Meanwhile, a signal received through the out-ear microphone 121 may be mixed with external noises, as well as the voices of the person. Accordingly, in the present invention, only the voices of the user are taken from the signal coming into the out-ear microphone 121, and high frequency part is extracted and used.

In the present invention, a signal close to the real voice of the user may be reproduced and a sound signal of high quality free from the noises can be acquired by mixing the low frequency components extracted using the in-ear microphone 111 with the high frequency components extracted in the steps of processing the signal received through the out-ear microphone 121.

Figure 2:
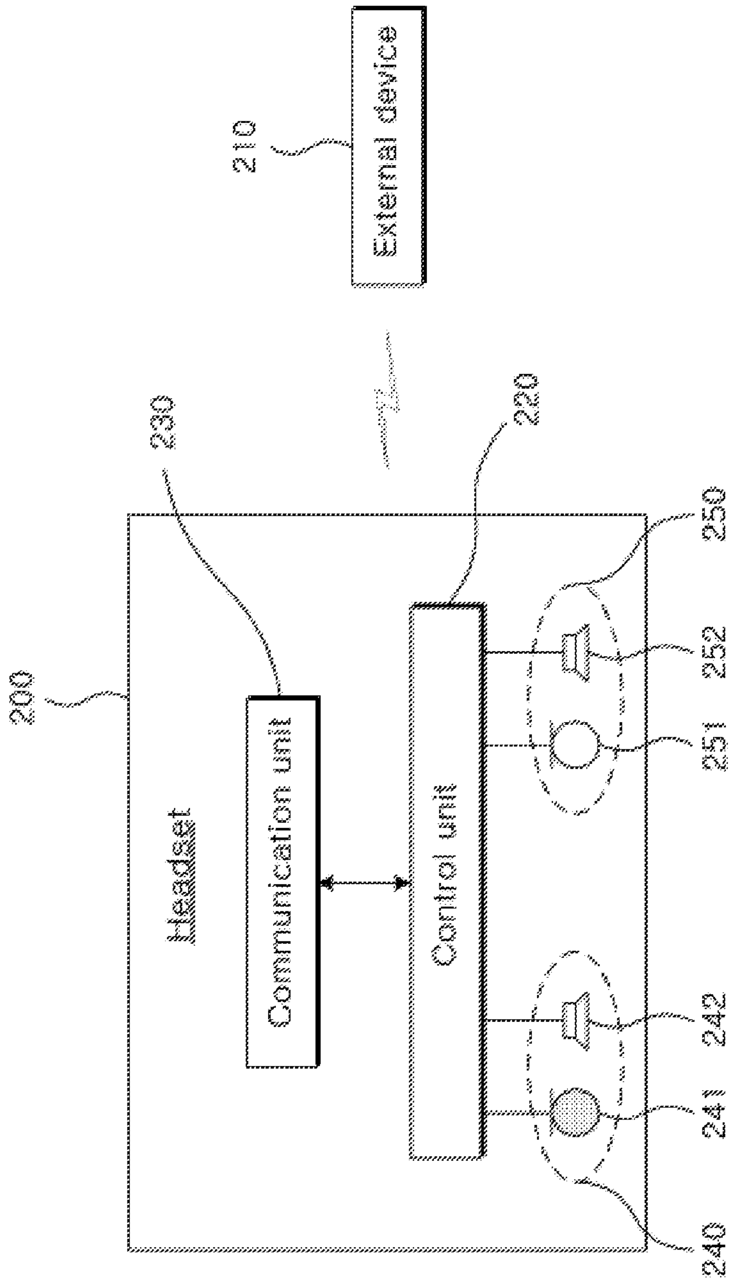
FIG. 2 is a functional block diagram showing the configuration of a headset according to an embodiment of the present invention.

FIG. 2 is a functional block diagram showing the configuration of a headset according to an embodiment of the present invention.

Referring to FIG. 2, a headset 200 is connected to an external device 210 such as a smart phone, a cellular phone or the like. The external device 210 is a computing device capable of transmitting a control signal and a sound signal to the headset 200 and receiving a sound signal through the microphones 241 and 251 of the headset 200, which will be a device having a sound information playback function, a communication function and/or a voice recognition function.

The external device 210 may be implemented as a cellular phone such as a smart phone or the like capable of using voice communication, short message service (SMS), data transmission and reception service and the like using a communication system, which has a camera for photographing a subject according to a request of a user and an MP3 player for playing back music according to a request of the user.

A wired or wireless communication method may be used for communication between the external device 210 and the headset 200, and although communication methods such as Bluetooth, Infrared, Zigbee and the like can be used, it is not limited to one of them.

Referring to FIG. 2, the headset 200 according to an embodiment of the present invention includes a first head 240 provided with an in-ear microphone 241 and a first speaker unit 242, a second head 250 provided with an out-ear microphone 251 and a second speaker unit 252, a communication unit 230 for communication with an external device 210, and a control unit 220 implemented in a circuit to perform an audio process of outputting a sound signal received through the communication unit 230 to the first speaker unit 242 and/or the second speaker unit 252, improving sound quality of a voice signal input through the microphones 241 and 251, and transmitting the voice signal to the external device 210 through the communication unit 230.

Figure 3:
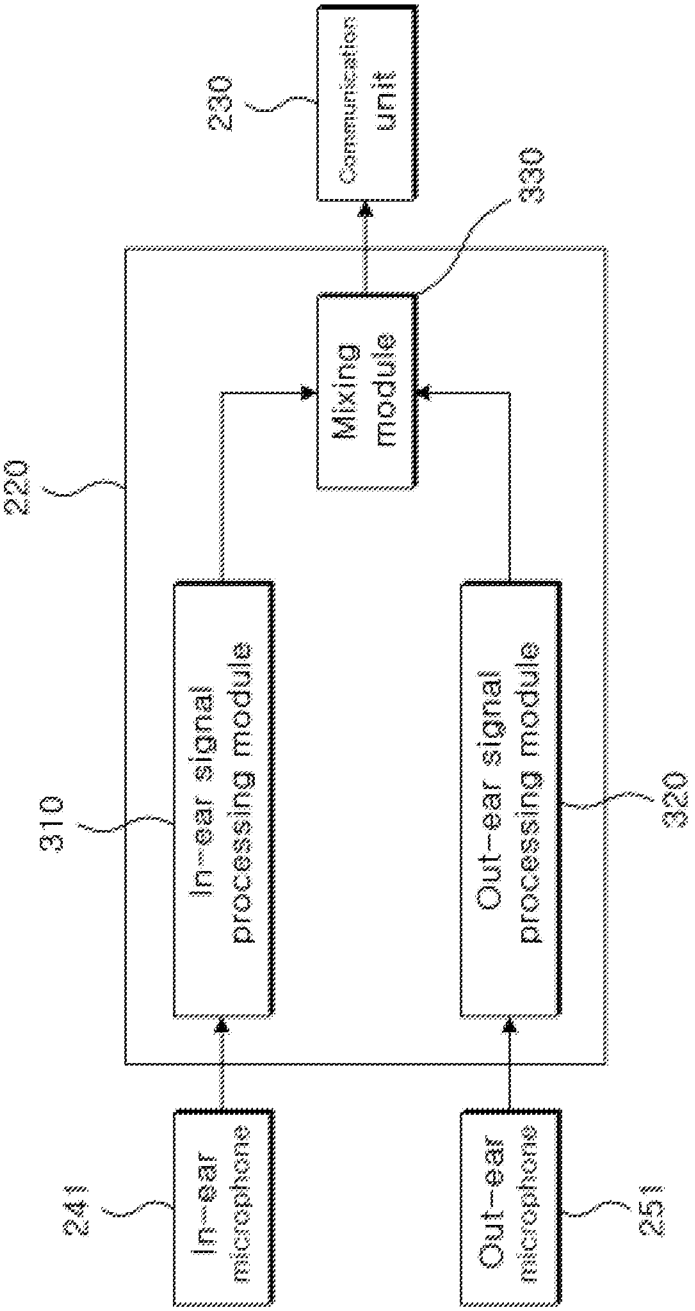
FIG. 3 is a functional block diagram showing the configuration of a control unit of a headset according to an embodiment of the present invention.

FIG. 3 is a functional block diagram showing the configuration of a control unit 220 of a headset according to an embodiment of the present invention.

Referring to FIG. 3, the control unit 220 may include an in-ear signal processing module 310 for extracting low frequency components from a signal sensed through the in-ear microphone 241, an out-ear signal processing module 320 for extracting high frequency components from a signal sensed through the out-ear microphone 251, and a mixing module 330 for mixing the extracted low frequency components and high frequency components and outputting the mixed signal.

The low frequency components extracted by the in-ear signal processing module 310 include low frequency signals lower than a first frequency, which is a predetermined frequency, and may be acquired in a method of filtering high frequency signals exceeding the first frequency.

The high frequency components extracted by the out-ear signal processing module 320 include high frequency signals higher than a second frequency, which is a predetermined frequency, and may be acquired in a method of filtering low frequency signals lower than the first frequency.

In addition, the signal output from the mixing module 330 of the control unit 220 will be transmitted to the external device through the communication unit 230.

Meanwhile, the present invention may be applied to a headset provided with a plurality of in-ear microphones and/or out-ear microphones.

If there is a plurality of in-ear microphones, quality of communication may be enhanced further more since the sound volume increases as the gain is improved. In this case, the low frequency signals extracted by the plurality of in-ear microphones may be mixed with each other to be used. The mixed low frequency signals will be mixed with the high frequency part extracted from the voice signal captured through the out-ear microphone.

Figure 4:
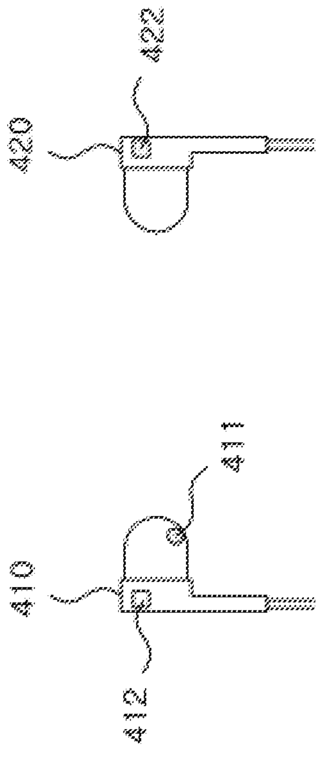
FIG. 4 is a view showing the outer appearance of a headset according to another embodiment of the present invention.
Figure 5:
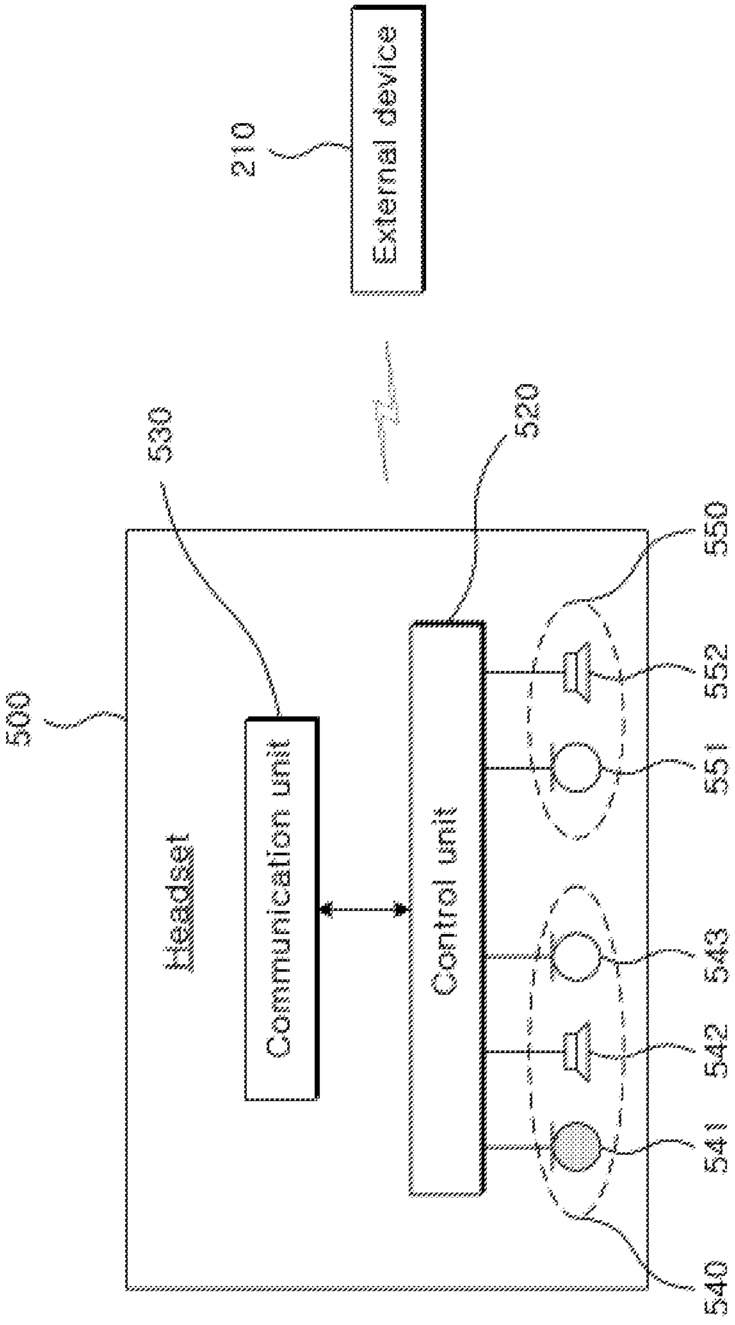
FIG. 5 is a functional block diagram showing the configuration of a headset according to another embodiment of the present invention.
Figure 6:
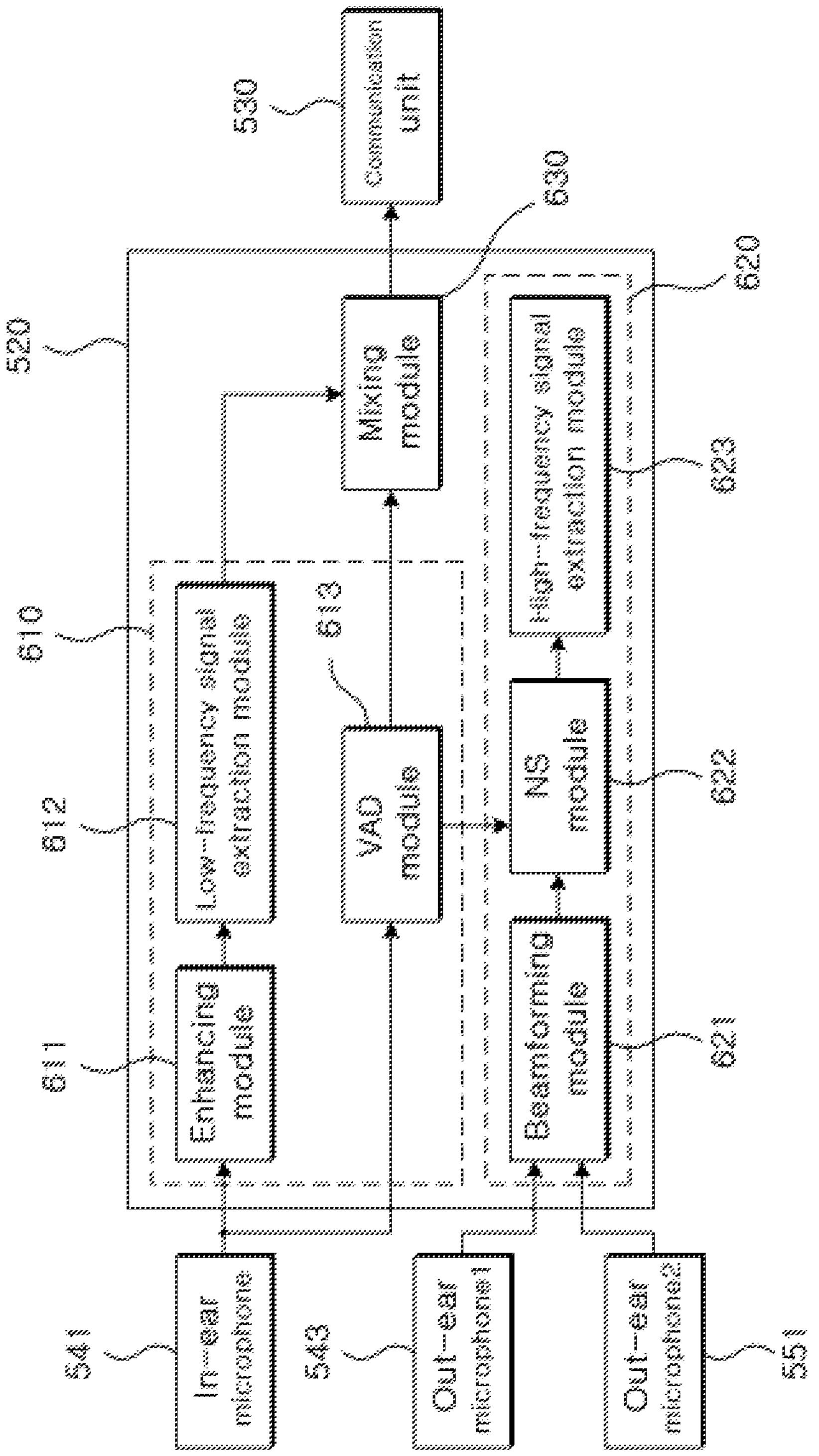
FIG. 6 is a functional block diagram showing the configuration of a control unit of a headset according to another embodiment of the present invention.

In addition, if there is a plurality of out-ear microphones, e.g., two out-ear microphones, signals may be processed as is described in the embodiment shown in FIGS. 4 to 6.

FIG. 4 is a view showing the outer appearance of a headset according to another embodiment of the present invention.

Referring to FIG. 4, a headset includes a first head 410 and a second head 420 worn in the ears of a user, and a speaker unit (not shown) is provided in each of the two heads 410 and 420. In addition, an in-ear microphone 411 and an out-ear microphone 412 are disposed in the first head 410 of the two heads, and an out-ear microphone 422 is disposed in the second head 420. That is, the out-ear microphones 412 and 422 are installed in both of the two heads 410 and 420.

FIG. 5 is a functional block diagram showing the configuration of a headset according to another embodiment of the present invention.

Referring to FIG. 5, a headset 500 is connected to an external device 210 such as a smart phone, a cellular phone or the like. A wired or wireless communication method may be used for communication between the external device 210 and the headset 500, and although communication methods such as Bluetooth, Infrared, Zigbee and the like can be used, it is not limited to one of them.

Referring to FIG. 5, the headset 500 according to an embodiment of the present invention includes a first head 540 provided with an in-ear microphone 541, a first speaker unit 542 and an out-ear microphone 543, a second head 550 provided with an out-ear microphone 551 and a second speaker unit 552, a communication unit 530 for communication with an external device 210, and a control unit 520 implemented in a circuit to perform an audio process of outputting a sound signal received through the communication unit 530 to the first speaker unit 542 and/or the second speaker unit 552, improving sound quality of a voice signal input through the microphones 541, 543 and 551, and transmitting the voice signal to the external device 210 through the communication unit 530.

FIG. 6 is a functional block diagram showing the configuration of a control unit 520 of a headset according to another embodiment of the present invention.

Referring to FIG. 6, the control unit 520 may include an in-ear signal processing module 610 for extracting low frequency components from a signal sensed through the in-ear microphone 541, an out-ear signal processing module 620 for extracting high frequency components from a signal sensed through the out-ear microphones 543 and 551, and a mixing module 630 for mixing the extracted low frequency components and high frequency components and outputting the mixed signal.

The in-ear signal processing module 610 may include an enhancing module 611 for balancing a signal by increasing the high frequency sound and decreasing the low frequency sound of a signal output from the in-ear microphone 541 before the low frequency components are extracted. Since a voice of a person includes high frequency components more than low frequency components, the signal is balanced by increasing the high frequency sound and decreasing the low frequency sound so that a counterpart may easily hear the sound.

In addition, the in-ear signal processing module 610 may include a low frequency signal extraction module 612 for extracting low frequency components from the signal balanced by the enhancing module 611. The extracted low frequency components include low frequency signals lower than a first frequency, which is a predetermined frequency, and may be acquired in a method of filtering high frequency signals exceeding the first frequency.

Meanwhile, the in-ear microphone 541 is mounted inside an ear of a user to capture only voices of a human without external noises, and if a signal comes in through the in-ear microphone 541, it may be determined that the user is in speaking. The in-ear microphone 541 may include a voice activity detection (VAD) module 613 for determining, if there is a signal sensed through the in-ear microphone 541, that the user is emitting a voice. The VAD module 613 outputs a voice sensing signal as a result of the determination, and the output voice sensing signal is applied to the mixing module 630 and/or a noise suppression module 622 so that mixing the high frequency components and the low frequency components and removal of the noises can be performed only while the user emits a voice.

The out-ear signal processing module 620 includes a configuration described below to take off only the voice of a user from a sound signal captured by the out-ear microphones 543 and 551 and extract only high frequency components from the voice.

The out-ear signal processing module 620 may include a beamforming module 621 for performing a beamforming process of sensing only a voice emitted from the user by removing a signal having a time difference from two signals output from the first out-ear microphone 543 and the second out-ear microphone 551. The beamforming is a technique of capturing only a sound of a specific direction, and if this technique is used, only a sound on the front side, i.e., a sound coming out from the mouth of the user, may be captured from two microphone signals. The two out-ear microphones 543 and 551 are mounted on corresponding positions of both heads, and in this case, they are positioned at the same distance from the mouth of the user in the opposite directions. The beamforming is a process of analyzing delay of the sound from the mouth of the user, which is the originating point of the sound, to both of the microphones 543 and 551 and removing all the signals having a time difference, and as a result, most of the noises coming in from the neighborhood, except the sound coming out from the mouth of the user, can be removed.

Noises can be removed from the signal output from the beamforming module 621 by the noise suppression (NS) module 622. At this point, consumption of power can be reduced by operating the NS module 622 only when it is determined by the VAD module 613 that the user is in speaking.

The out-ear signal processing module 620 may further include a high frequency signal extraction module 623 for extracting only high frequency components from the noise-free signal output from the NS module 622, and at this point, the extracted high frequency components include high frequency signals higher than a second frequency, which is a predetermined frequency, and may be acquired in a method of filtering low frequency signals lower than the second frequency.

The control unit 520 includes the mixing module 630 for mixing the low frequency components output from the low frequency signal extraction module 612 and the high frequency components output from the high frequency signal extraction module 623, and a signal output from the mixing module 630 will be transmitted to an external device through the communication unit 540. The signal output from the mixing module 630 will be a signal close to a real voice of the user. In addition, consumption of power can be reduced by operating the mixing module 630 only when it is determined by the VAD module 613 that the user is in speaking.

Figure 7:
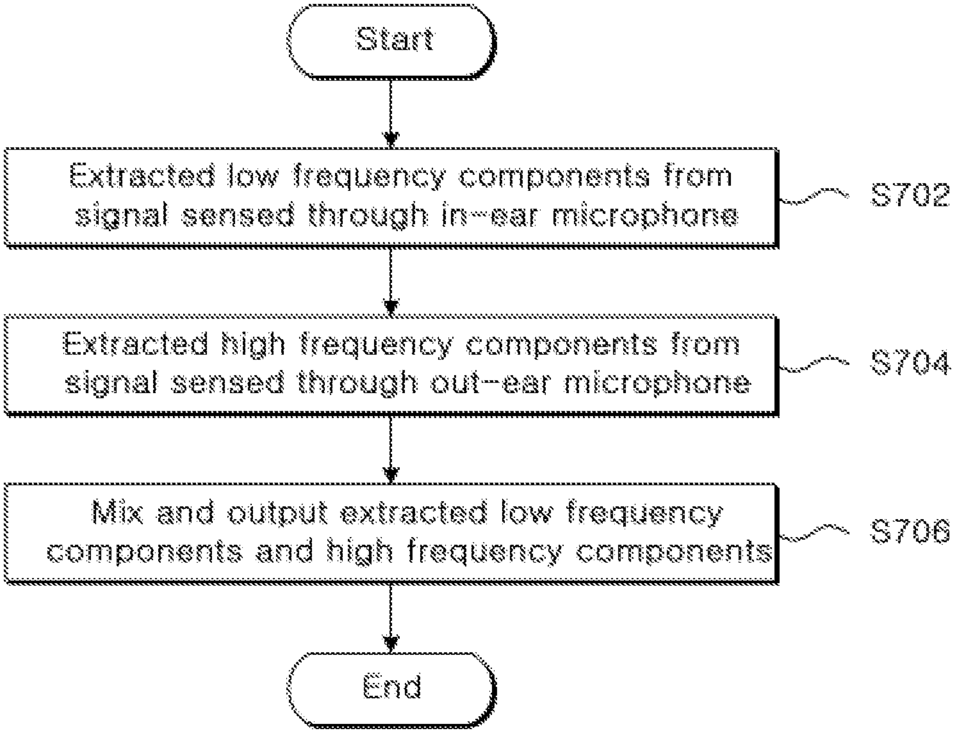
FIG. 7 is a flowchart illustrating a method of improving sound quality of a headset according to another embodiment of the present invention.

FIG. 7 is a flowchart illustrating a method of improving sound quality of a headset according to another embodiment of the present invention.

Referring to FIG. 7, low frequency components are extracted from a signal sensed through the in-ear microphone (step S702), and high frequency components are extracted from a signal sensed through the out-ear microphone (step S704). Next, the extracted low frequency components and high frequency components are mixed and output (step S706). The detailed process performed at each step is as described above with reference to FIGS. 1 to 6.

The method according to an embodiment of the present invention may be implemented in the form of a program command that can be executed through various computer means and recorded in a computer-readable recording medium. The computer-readable recording medium may include a program command, a data file, a data structure and the like solely or in a combined manner. The program command recorded in the computer-readable recording medium may be a program command specially designed and configured for the present invention or a program command known to by those skilled in the art to be used. The computer-readable recording medium includes, for example, a magnetic medium, such as a hard disk, a floppy disk and a magnetic tape, an optical recording medium, such as a CD-ROM and a DVD, a magneto-optical medium, such as a floptical disk, and a hardware device specially configured to store and execute program commands, such as a ROM, a RAM, a flash memory and the like. The program command includes, for example, a high-level language code that can be executed by a computer using an interpreter or the like, as well as a machine code generated by a compiler.

Although embodiments of the present invention have been described in detail, the scope of the present invention is not limited thereto, but various modifications and improved forms made by those skilled in the art using the basic concept of the present invention defined in the appended claims belong to the scope of the present invention.

The invention claimed is:

1. A headset comprising:

at least one in-ear microphone;

at least one out-ear microphone;

a control unit including:

an in-ear signal processing module for extracting low frequency components from a signal sensed through the in-ear microphone, an out-ear signal processing module for extracting high frequency components from a signal sensed through the out-ear microphone, and a mixing module for mixing the extracted low frequency components and high frequency components and outputting the mixed signal; and a communication unit for transmitting the signal output from the mixing module of the control unit to an external device;

wherein the at least one out-ear microphone includes a first out-ear microphone provided in a first head of the headset and a second out-ear microphone provided in a second head of the headset, and the out-ear signal processing module includes a beamforming module for performing a beamforming process of sensing only a voice emitted from a user by removing a signal having a time difference from two signals output from the first out-ear microphone and the second out-ear microphone;

wherein the out-ear signal processing module further includes a noise suppression module for removing noises from a signal output from the beamforming module; and wherein the in-ear signal processing module includes a voice activity detection (VAD) module for determining, if there is a signal sensed through the in-ear microphone, that a user is emitting a voice, and the noise suppression module operates only when it is determined by the VAD module that the user is emitting a voice.

2. The headset according to claim 1, wherein the in-ear signal processing module includes a voice activity detection (VAD) module for determining, if there is a signal sensed through the in-ear microphone, that a user is emitting a voice, and the mixing module operates only when it is determined by the VAD module that the user is emitting a voice.

3. The headset according to claim 1, wherein the in-ear signal processing module includes an enhancing module for balancing a signal by increasing a high frequency sound and decreasing a low frequency sound of a signal output from the in-ear microphone before the low frequency components are extracted.

4. A method of improving sound quality of a headset provided with at least one in-ear microphone and at least one out-ear microphone, the method comprising the steps of:

extracting low frequency components from a signal sensed through the in-ear microphone;

extracting high frequency components from a signal sensed through the out-ear microphone; and mixing and outputting the extracted low frequency components and high frequency components;

wherein before the step of extracting high frequency components, performing a beamforming process of extracting only a voice emitted from a user by removing a signal having a time difference from signals output from a first out-ear microphone provided in a first head of the headset and a second out-ear microphone provided in a second head of the headset;

determining, if there is a signal sensed through the in-ear microphone, that the user is emitting a voice; and removing noises from a signal output as a result of performing the beamforming process, wherein the step of removing noises is performed only when it is determined that the user is emitting a voice.

5. The method according to claim 4, wherein further comprising, before the step of extracting low frequency components, the enhancing step of balancing a signal by increasing a high frequency sound and decreasing a low frequency sound of a signal output from the in-ear microphone.

* * * * *